United States Patent [19]
Grüning

[11] Patent Number: 6,030,939
[45] Date of Patent: Feb. 29, 2000

[54] AQUEOUS PREPARATIONS CONTAINING BETAINES BASED ON POLYMERIC FATTY ACIDS

[75] Inventor: Burghard Grüning, Essen, Germany

[73] Assignee: Th. Goldschmidt AG, Essen, Germany

[21] Appl. No.: 09/266,365

[22] Filed: Mar. 11, 1999

Related U.S. Application Data

[63] Continuation of application No. 08/092,341, Jul. 15, 1993, abandoned.

[30] Foreign Application Priority Data

Aug. 19, 1992 [DE] Germany ................................ 4227391

[51] Int. Cl.$^7$ .................. C11D 1/90; C11D 7/10
[52] U.S. Cl. ..................... 510/490; 510/123; 510/433
[58] Field of Search .................. 510/123, 490, 510/433

[56] References Cited

U.S. PATENT DOCUMENTS 4,582,636  4/1986  Crossin .................................. 252/546

OTHER PUBLICATIONS

Chemical Abstracts vol. 112, #22,799a; Surface active low foaming amido betaines for use in laundry detergents; Krob et al, Jan. 22, 1990.

Chemical Abstracts: vol. 112, No. 4, Jan. 22, 1990.

Primary Examiner—Yogendra Gupta
Assistant Examiner—Charles Boyer
Attorney, Agent, or Firm—Frommer Lawrence & Haug LLP

[57] ABSTRACT

An aqueous, flowable preparation contains 5 to 30% by weight of a mixture of betaines, which consists of 15 to 60% by weight of betaines based on fatty acid amides of fatty acids with 8 to 18 carbon atoms, 85 to 40% by weight of betaines based on polymer acid amides; and 95 to 70% by weight of water, alkali salts and optionally conventional additives, such as solubilizers, preservatives, etc. The preparation, optionally after admixture with other surfactants, is suitable particularly as detergents and cleaning agents for personal grooming, as auxiliaries in the textile industry and as cleaning agents for technical purposes.

11 Claims, No Drawings

AQUEOUS PREPARATIONS CONTAINING BETAINES BASED ON POLYMERIC FATTY ACIDS

RELATED APPLICATIONS

This application is a continuation of U.S. application Ser. No. 08/092,341, filed on Jul. 15, 1993, now abandoned which claims priority of German Patent Application P 42 27 391.9, filed Aug. 19, 1992, herein incorporated by reference.

FIELD OF INVENTION

The present invention relates to preparing aqueous solutions of betaines based particularly on dimer and trimer acids which are still liquid even at higher concentrations. The aqueous solution should be as low foaming as possible so that these polymer acid betaines can be used for technical applications.

BACKGROUND INFORMATION AND PRIOR ART

Betaines of the general formula

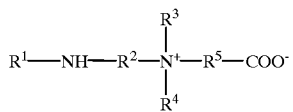

I wherein
- $R^1$ is an acyl group of a fatty acid with 8 to 18 carbon atoms,
- $R^2$ is a divalent, aliphatic hydrocarbon group with 2 to 5 carbon atoms,
- $R^3$, $R^4$ independently of one another are aliphatic hydrocarbon groups with 1 to 4 carbon atoms, and
- $R^5$ is the —$CH_2$— or —$(CH_2)_2$— group, have long been known. They are described in various patents, of which the German Auslegeschrift 10 62 393 is an example.

Betaines are used as amphoteric surfactants, particularly for hair- and skin-cleaning preparations, such as shampoos, foam and shower gels gentle to the skin, feminine hygiene and skin care products. They improve the dermatological properties of anionic surfactants and cause skin to be pleasant to touch. In addition, the betaines can be used as surfactants for industrial purposes, for example, in the textile industry, or as anticorrosive agents in metal-treating liquids.

The betaines of the state of the art are distinguished by their high foaming ability, the foam being stable even in the presence of salts which are dissolved in water and cause it to be hard. As desirable as this foaming tendency may be for many applications, it does interfere with some uses, so that the availability of low foaming betaines is desirable particularly if these betaines are used for technical purposes.

The Czechoslovakian Patent 260933 disclosed betaines, the fatty acid group of which is derived from dimer and trimer fatty acids. Such polymeric fatty acids are commercially available under the name of dimer and trimer acids. The dimer acids are a mixture of dicarboxylic acids with a total of, generally, 36 carbon atoms, which are synthesized by covalently linking unsaturated fatty acids with 18 carbon atoms at temperatures above 200° C., generally in the presence of clay minerals. Oleic acid, linoleic acid and linolenic acid are generally used as unsaturated fatty acids. The dimer acids, obtained in this manner, can subsequently be hydrogenated.

With regard to the synthesis and use of dimer acids and their physical and chemical properties, reference is made to the publication: "The Dimer Acids: The chemical and Physical Properties, Reactions and Applications", edited by E. C. Leonard; Humko Sheffield Chemical, 1975, Memphis, Tenn.

The dimer acid can correspond to the following formula:

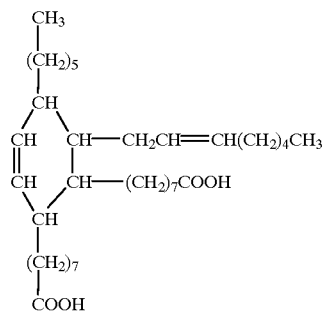

The trimer acids are synthesized in a similar manner and are tricarboxylic acids which are obtained by the trimerization of unsaturated fatty acids and generally contain 54 carbon atoms.

These polymer acids are obtainable commercially in different degrees of purity, because the crude reaction product, resulting from the dimerization of unsaturated $C_{18}$ fatty acids, contains, aside from dimer acid, trimer acid of the monomeric carboxylic acids and appreciable amounts of intermediates of unknown structure, the molecular weight of which ranges from $C_{18}$ to $C_{36}$. If betaines are synthesized using polymer acids, it is noted that, as the purity of the polymer acids increases, the viscosity of their aqueous solutions increases greatly at comparable concentrations until said solutions finally become gelatinous and are no longer free flowing. For example, when crude dimer and trimer acid mixtures are used, it is possible to prepare betaine solutions with a solids content of about 15 to 25% by weight. However, if purified, particularly distilled dimer acids are used, the aqueous solutions become already solid at solids contents above about 4 to 5% by weight. This limits the usability of such betaines based on dimer acid. Particularly for cosmetic applications, but also in numerous technical applications, such as the treatment of textiles, the use of rather pure substances, which are well defined, is aimed for in order to keep toxicological risks as small as possible. Therefore betaines especially based on purified polymer fatty acids are particularly important.

It is known to mix betaines, which were synthesized separately using different fatty acids, after their synthesis in order to obtain particular application properties. For example, the EP-A2 0 121 791 discloses a preparation for cosmetic formulations, which contains a mixture of coconut oil amidopropylbetaine and oleoamidopropylbetaines in the ratio of 1:4 to 3:2. This betaine mixture has thickening and foam-reinforcing properties in aqueous cosmetic preparations and shows improved emulsifying properties, for example, for jojoba oil.

OBJECT OF THE INVENTION

An object of the present invention is preparing aqueous solutions of betaines based particularly on dimer and optionally on trimer acids, which are still liquid even at higher concentrations. The aqueous solution should be as low foaming as possible so that these polymer acid betaines can also be used particularly for technical applications.

SUMMARY OF THE INVENTION

Surprisingly, it was found that these properties may be encountered in an inventive preparation, which is characterized by containing
5 to 30% by weight of a mixture of betaines, which consists of 15 to 60% by weight of betaines of the general formula

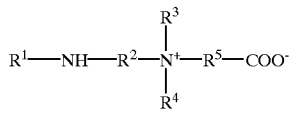

and
85 to 40% by weight of betaines of the general formula,

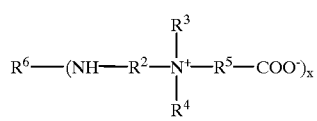

the percentages by weight adding up to 100% by weight, wherein
- $R^1$ is an acyl group of a fatty acid with 8 to 18 carbon atoms or a mixture of these fatty acids,
- $R^2$ is a divalent aliphatic hydrocarbon group with 2 to 5 carbon atoms,
- $R^3$, $R^4$ independently of one another are aliphatic hydrocarbon groups with 1 to 4 carbon atoms,
- $R^5$ is the —$CH_2$— or —$(CH_2)_2$ group,
- $R^6$ is the acyl group of a polymer fatty acid with x acyl groups,
- x is a number from 2 to 5 and 95 to 70% by weight of water, alkali metal salts and optionally conventional additives such as auxiliary solvent, preservatives, etc.
- $R^1$ preferably is the acyl group of a fatty acid mixture with, on the average, about 12 to 14 carbon atoms, such as the mixture of coconut oil fatty acids.
- $R^2$ preferably is an alkylene group having the formula —$(CH_2)_2$— or —$(CH_2)_3$—.
- $R^3$ and $R^4$ preferably are methyl groups.
- $R^5$ preferably is the —$CH_2$—.
- $R^6$ preferably is an acyl group of the dimer acid.

Particularly preferred are distilled dimer acids, such as those commercially obtainable under the name PRIPOL 1012/1013 and, in hydrogenated form, under the name PRIPOL 1008/1009 (from the Unichema Company). They contain only small proportions (less than 0.1% by weight) of monobasic acids and (less than 5% by weight) of trimer acids and have, particularly in the hydrogenated form, a bright color. In this case, subscript x has a value of 2. It is, of course, also possible to use dimer acids, the trimer acid content of which is higher. However, the limiting concentration, above which the aqueous solutions of the betaine mixture are no longer flowable, then falls.

Inventive preparations, in which $R^1$ is the acyl group of a coconut oil fatty mixture and $R^6$ the acyl group of a distilled dimer acid, are still flowable within the limits given in the present application at a solid content of up to 30% by weight. The preparations are low-foaming and therefore particularly useful for technical purposes.

The inventive preparations can be employed for many industrial purposes. A particular preferred application is their use in the textile industry. The betaine mixtures show high substantivity for fibers. When used on wool, the bonding length of the wool is increased. The bonding length is understood to be the length of the wool yarn above which the yarn breaks under its own weight.

The decreased foaming makes it possible to use the inventive betaine mixtures in detergents and cleaning agents which are intended to be used in washing machines. The inventive betaine mixtures improve the properties of detergents overall, particularly inasmuch as they decrease the bleeding of dyes and improve the handle of washed textiles.

The inventive mixtures are also suitable for other technical application. They can be used as dispersants for pigments in dyes, lacquers and paints and prevent or reduce the tendency of pigments to deposit in such products or facilitate the re-dispersal of such pigments. In metal processing liquids, such as drilling or cutting oil emulsions, they decrease the corrosivity of the aqueous preparations. They can also be used in various ways as antistats.

Other possible uses are in cosmetic preparations. Betaine mixtures produce a conditioning of the hair when they are employed, for example, in a shampoo or a dry-hair lotion. As a result, the hair develops a pleasant handle and an improved strength. The betaine mixtures are surfactant preparations with a very low irritation potential. They are therefore suitable for preparing particularly mild cosmetic formulations. When the inventive betaine mixtures are used in shampoos and toiletry soaps, it turns out that the viscosity of the aqueous preparations, consisting of anionic surfactants, such as sodium lauryl ether sulfate, and electrolytes, such as alkali metal chlorides, can be increased more than with conventional betaines. This, however, also means that the same viscosity can be achieved with lesser additions of anionic surfactants and/or smaller contents of electrolytes.

In technical, as well as, particularly in cosmetic applications, the betaine preparations based on polymer fatty acids are not used alone, but preferably in admixture with other active ingredients. Such active ingredients are primarily:

(1) anionic surfactants, such as fatty alcohol sulfates, fatty alcohol ether sulfates, alkylsulfonates, aklylbenzenesulfonates, alkyl esters of sulfosuccinic acid and, furthermore (2) nonionic surfactants, such as fatty acid esters of glycerin or sorbitol, which optionally can additionally be alkoxylated, fatty alcohol ethoxylates, fatty acid ethoxylates, fatty acid alkanolamides, polyalkylene glycols, fatty acid sugar esters, fatty acid glucoside esters, alkyl glucosides, as well as (3) amphoteric surfactants, such as betaines and amphol glycinates, and (4) cationic surfactants.

Possible other active ingredients and additives of such formulations are: Kaolin, bentonite, fatty acids, higher fatty alcohols, vaseline or paraffin oil, thickeners, such as ethoxylated fatty acid derivatives, starch, polyacrylic acid and its derivatives, cellulose derivatives, alginates, and furthermore opacifiers such as glycol ester derivatives, alcohols such as ethanol, propanol, propylene glycol or glycerin, solubilizers, stabilizers, buffers, perfume oils, dyes, as well as conditioning and grooming components, such as cationic or amphoteric polymers, protein hydrolysates, lanolin derivatives, cholesterol, pantothenic acid and polydimethyl siloxanes and their derivatives.

Because of their low irritation potential, the inventive betaine mixtures are furthermore suitable for use in cleansing agents which come into contact with skin during their use, such as dishwashing detergents and other cleansing, grooming and polishing agents.

In the following examples, the synthesis of betaine mixtures and their application properties are shown in even greater detail, it being understood that the following examples are given by way of illustration and not by way of limitation.

I. Synthesis of the Amidamines Required as Starting Materials

Not of the Invention

Dimer acid (56 g), obtainable commercially under the name PRIPOL 1009 and having an acid number of 204, is heated for about 4 hours under a steady, slow stream of nitrogen together with 26.4 g of dimethylaminopropylamine, the temperature being raised slowly from 140° C. to 200° C. The water formed as well as the excess amine is carried out with the nitrogen. The reaction is finished when the acid number of the reaction product is less than 4.

II. Synthesis of the Inventive Betaine Mixtures

EXAMPLE II (1)

Dimer acid amidamine (34 g) from dimer acid and dimethylaminopropylamine and 28.8 g of coconut oil fatty acid amidamine from coconut oil fatty acids and dimethylaminopropylamine are heated to 60° C. and treated with a solution of 19.2 g of sodium chloroacetate in 343 g of water. The reaction mixture is kept for 5 hours at a temperature of 95° C. and a Ph of more than 8.5. By means of thin-layer chromatography, it is established that the conversion is better than 95%. The product contains 19.3% solids and 2.3% sodium chloride. The substance with detergent activity (WAS) is composed of equal parts by weight of dimer acid betaine and coconut oil fatty acid betaine (each 8.5%). The product is a clear, slightly yellowish, flowable, viscous, aqueous solution with weakly pronounced viscoelastic properties.

In a similar manner, the betaine mixtures II 2 to II 5 are synthesized; they differ, among other things, in their composition. The composition and viscosity are listed in the following Table 1.

III. Properties of the Inventive Betaine Mixtures

Foaming Behavior

EXAMPLE III (1)

A modified Ross-Miles method of DIN 53 902 is used to determine the foaming capability. For this method, the run-out time and foam height of 500 mL of a solution of the sample in water from a defined height onto the liquid surface of the same solution are measured 30 seconds, 3 minutes and 5 minutes after such a solution has flowed out freely.

The product of Example II 1 is investigated. In addition, the foaming behavior of a mixture with sodium lauryl ether sulfate (commercially obtainable under the name TEXAPON N25) is checked. The foaming ability of the pure surfactants, coconut oil fatty acid amidopropyl betaine and sodium lauryl ether sulfate, are given for comparison.

The temperature of the solutions to be investigated is 45° C. and the concentration of substance with surfactant activity is 0.015%. The results are summarized in the following Table 2.

TABLE 2

| Product | Water 0° DH | | Water 16.8° DH | |
|---|---|---|---|---|
| | Time (min.) | Foam Height (mm) | Time (min.) | Foam Height (mm) |
| Product of Example II 1 (of the invention) | 0.5 | No foam | 0.5 | No foam |
| Coconut oil fatty acid betaine (not of the invention) | 0.5 | 100 | 0.5 | 100 |
| | 3 | 90 | 3 | 90 |
| | 5 | 85 | 5 | 85 |
| Product of Example II 1 (0.003% WAS) + sodium lauryl ether sulfate (0.012% WAS) | 0.5 | 100 | | |
| | 3 | 90 | | |
| | 5 | 88 | | |
| Sodium lauryl ether sulfate (not of the invention) | 0.5 | 140 | | |
| | 3 | 130 | | |
| | 5 | 127 | | |

The results show the low foaming ability of the betaine mixture. Foam formation by the anionic surfactant, sodium lauryl ether sulfate, is clearly reduced.

TABLE 1

| Example | II 1 | II 2 | II 3 | II 4 | II 5 | Comparison Example |
|---|---|---|---|---|---|---|
| Content of coconut oil fatty acid betaine (%) | 4.2 | 6.3 | 2.0 | 2.5 | 5.2 | — |
| Quality of polymer acid betaine | Dimer[1]) acid distilled | Dimer[1]) acid distilled | Dimer[1]) acid distilled | Dimer[2]) acid not distilled | Trimer[3]) acid | Dimer[1]) acid distilled |
| Content of polymer acid betaine (%) | 12.8 | 18.6 | 11.2 | 20.0 | 14.8 | 5 |
| Total content of betaine (%) | 17 | 24.9 | 13.2 | 22.5 | 20 | 5 |
| Viscosity, 25° C. (mPas) | 4000 | 150 | 9700 | 1000 | 550 | not flowable |
| pH (25° C.) | 6.5 | 6.5 | 6.5 | 6.5 | 6.5 | 6.5 |

Polymer acid betaine raw material:
[1])Unichema PRIPOL 1009
[2])Unichema PRIPOL 1017
[3])Unichema PRIPOL 1040

EXAMPLE III (2)
Improvement in the Bond Length of Wool

The bond lengths provide information concerning fiber—fiber frictional behavior.

| Substrate: | wool, worsted top |
|---|---|
| Fineness: | 21.7 μm |
| Length: | 67 mm |
| Test Substance: | betaine mixture of Example II (2) |

The bond length is determined by a method based on DIN 53 834: "Simple Tensile Test on Yarns and Plied Yarns". On a worsted top, 0.3% by weight (based on the active substance) of the betaine mixture is applied from an aqueous dilution by spraying. After drying and conditioning for 36 hours at 65% R.H. and 20° C., the combed slivers are stretched twice on a gill box into drafter slivers. The weight of the drafter slivers is 9.17 g/m. Test specimens, 200 mm in length (corresponding to 3 times the staple length) are cut off from the drafter slivers. These test specimens are subjected to a tensile test in a Zwick Universal Testing Machine (Germany) at a test rate of 500 mm/min. The highest point in the forced-elongation curve corresponds to the maximum bonding force and represents the static fiber-to-fiber friction. From the force measured in this experiment and the weight of the drafter sliver, the length (bond length) is calculated, at which the drafter sliver would tear under its own weight.

The following results are obtained:

| Untreated wool: | 28.1 m |
|---|---|
| Wool treated with betaine: | 38.0 m |

The bond length of the wool is clearly improved by use of the betaine mixture.

EXAMPLE III (3)
Shampoo Formulation

A hair shampoo is produced from the following materials:

| Sodium lauryl ether sulfate[1]: | 12.0% by weight of active substance |
|---|---|
| Coconut oil fatty acid amidopropyl-betaine[2]: | 3.0% by weight of active substance |
| Betaine mixture of Example II 2: | 4.0% by weight of active substance |
| NaCl: | 0.5% by weight |
| Water: | 80.5% by weight |

[1] from Texapon N 25
[2] from TEGO Betain L7

The components are mixed together in the order given.

The formulation is clear, slightly yellowish and has a viscosity of 7,500 mPas and a pH of 6.5. Hair, washed with this shampoo formulation, is pleasant to the touch and can be combed clearly better than the hair which has been washed with a comparable shampoo formulation without dimer betaine.

I claim:

1. An aqueous free-flowing preparation comprising betaines based on fatty acid amides and polymeric acid amides, said mixture comprising 5 to 30% by total weight of the mixture, a mixture of betaines consisting of 15 to 60% by weight of betaines of the formula

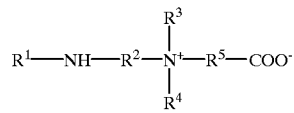

$$R^1\text{---}NH\text{---}R^2\text{---}\underset{\underset{R^4}{|}}{\overset{\overset{R^3}{|}}{N^+}}\text{---}R^5\text{---}COO^- \quad (I)$$

and 85 to 40% by weight of betaines of the formula

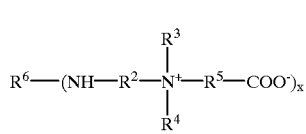

$$R^6\text{---}(NH\text{---}R^2\text{---}\underset{\underset{R^4}{|}}{\overset{\overset{R^3}{|}}{N^+}}\text{---}R^5\text{---}COO^-)_x \quad (II)$$

the % by weight adding up to 100% by weight, where $R^1$ is the acyl radical of a fatty acid having from 8 to 18 carbon atoms or a mixture of such fatty acids, $R^2$ is a divalent aliphatic hydrocarbon radical having from 2 to 5 carbon atoms, $R^3$, $R^4$ independently of one another are aliphatic hydrocarbon radicals having from 1 to 4 carbon atoms, $R^5$ is the —$CH_2$— radical or —$(CH_2)_2$—, $R^6$ is an acyl radical derived from distilled dimer acid, and x is a number from 2 to 5, and 95 to 70% by weight of water.

2. The preparation according to claim 1, which further comprises solvents or preservatives.

3. The preparation according to claim 1, which further comprises an anionic surfactant, a nonionic surfactant, an amphoteric surfactant or a cationic surfactant.

4. The preparation according to claim 1, which further comprises an alkali metal salt and the alkali metal salt is sodium chloride.

5. The preparation of claim 1, wherein the $R^2$ group is a —$(CH_2)_2$— or —$(CH_2)_3$— group.

6. The preparation of claim 4, wherein the $R^3$ and $R^4$ groups are methyl groups.

7. The preparation of claim 1, wherein the $R^5$ group is a —$CH_2$— group.

8. The preparation of claim 1, comprising that the $R^1$ group is an acyl group derived from the coconut oil fatty acid mixture.

9. An agent to increase bonding length of a textile fiber comprising an effective amount of the preparation of claim 1, said bonding length being the length of the yarn comprising the fiber above which the yarn breaks under its own weight.

10. A cleaning agent or detergent comprising a detersive effective amount of the preparation of claim 1.

11. A dispersing agent for pigments in dyes, lacquers or paints comprising an effective amount of the preparation of claim 1.

* * * * *